US006191111B1

(12) United States Patent
Leschinsky

(10) Patent No.: US 6,191,111 B1
(45) Date of Patent: Feb. 20, 2001

(54) METHOD AND DEVICE FOR ENHANCING OF BIOBYPASS BY INCREASING THE CORONARY BLOOD FLOW

(75) Inventor: Boris Leschinsky, Waldwick, NJ (US)

(73) Assignee: Datascope Investment Corp., Montvale, NJ (US)

( * ) Notice: Under 35 U.S.C. 154(b), the term of this patent shall be extended for 0 days.

(21) Appl. No.: 09/251,499

(22) Filed: Feb. 17, 1999

(51) Int. Cl.$^7$ .............................. A61K 38/00; A61B 5/00; A61M 29/00
(52) U.S. Cl. .............................. 514/12; 530/399; 600/18; 601/152; 606/194
(58) Field of Search .............................. 514/12; 530/399; 600/18; 601/152; 606/194

(56) References Cited

U.S. PATENT DOCUMENTS 5,554,103 * 9/1996 Zherg et al. .......................... 601/152
5,716,373 * 2/1998 Wolvek et al. ....................... 606/194

OTHER PUBLICATIONS

Yanagisawa–Miwa et al, *Science*, vol. 257, pp. 1401–1403, 1992.*
J. Ando et al. Blood Flow and Vascular Endothelial Cell Function. Frontiers Med Biol Engng 1993;5:245–264.
W. Risau. Mechanisms of Angiogenesis. Nature 1997;386:671–674.
F. Bussolino, et al. Molecular Mechanisms of Blood Vessel Formation. TIBS 1997;22:251–256.
W. Schapner et al. Molecular Mechanisms of Coronary Collateral Vessel Growth. Circulation Research 1996;79:911–919.
A Yanadisawa–Miwa et al. Salvage of Infarcted Myocardium by Angiogenic Action of Basic Fibroblast Growth Factor. Science 1992;257:1401–1403.
K. Harada et al. Basic Fibroblast Growth factors Improves Myocardial Function in Chronically Ischemic Porcine Hearts. J Clin Invest 1994;94:623–630.
D. Lazarous et al. Effects of Chronic Systemic Administration of Basic Fibroblast Growth Factors on Collateral Development in the Canine Heart. Circulation 1995;91:145–153.
A. Ware et al. Angiogenesis in Ischemic Heart Disease. Nature Medicine 1997;3:158–164.
F. Giordano et al. Intracoronary Gene Transfer of Fibroblast Growth Factor—5 Increases Blood Flow and Contractile Function in an Ischemic Region of the Heart. Nature Medicine 1996;2:534–539.
D. Losorto et al. Gene Therapy for Myocardial Angiogenesis. Intitial Clinical Results with Direct Myocardial Injection of ph $VEGF_{165}$ as Sole Therapy for Myocardial Ischemia. Circulation 1998;98:2800–2804.
N. Yamamoto et al. Angiogenesis is Enhanced in Ischemic Canine Myocardium by Transmyocardial Laser Revascularization. J Am Coll Cardiol 1998;31:1426–1433.

* cited by examiner

Primary Examiner—Christopher S. F. Low
Assistant Examiner—Abdel A. Mohamed
(74) Attorney, Agent, or Firm—Boris Leschinsky

(57) ABSTRACT

A method for enhancing such biobypass techniques as angiogenesis, trans-myocardial revascularization, percutaneous myocardial revascularization, and myocardial cell proliferation by using the means for increasing of coronary blood flow to both instantly relieve the ischemic symptoms and stimulate the growth of new blood vessels. Intra-aortic balloon pumping and other counterpulsation means are identified as preferred means for increasing of coronary blood flow.

11 Claims, No Drawings

METHOD AND DEVICE FOR ENHANCING OF BIOBYPASS BY INCREASING THE CORONARY BLOOD FLOW

BACKGROUND OF THE INVENTION

1. Field of the Invention

The present invention relates to a device and a method for treating ischemic conditions of major organs in the human body. More particularly, the method and the device of the invention relate to the treatment of the heart disease caused by reduction in myocardial blood flow due to the narrowing of the native coronary blood vessels or occlusion of the bypass grafts.

2. Description of the Related Art

Cardiac failure remains one of the leading causes of death in the United States. At the present time, there are two conventional methods of treatment of the cardiac disease at its advanced stage: 1. Coronary artery bypass graft (CABG) surgery is used to mechanically bypass the area of coronary obstruction, and 2. Various interventional cardiology techniques such as percutaneous transluminal coronary angioplasty (PTCA) or intra-coronary stents designed to open up the narrowing vessels to restore adequate blood flow.

The advantages and high success rate of both techniques are widely known. Many of the patients can benefit significantly from either one of these approaches. However, there is a significant number of patients, between 3 to 6 percent according to some estimates, with so-called "diffused" disease where the obstruction of the vessel tree is not limited to a small well defined area and thus can not be treated with existing techniques. In addition, up to 15 percent of cardiac patients have some degree of "diffused" coronary disease and can be only partially revascularized by conventional means.

Many alternative treatment methods are under development for these patients. Once proven in this patient population group, these methods may be widely used for other cardiac patients as well. For the purposes of this description, the term "biobypass" is used to describe broadly these alternative treatments.

The essence of the approach is to promote the growth of new blood vessels to "biologically bypass" the areas of restriction in the coronary vessel tree. This approach is generally known as angiogenesis. Another possible implementation of biobypass is restoring the contractile function of the myocardium by transplanting healthy myocardial cells, or myocytes, in the areas of the heart damaged by the infarction process. The following is a more detailed description of these biobypass techniques as it relates to the method of the present invention.

Angiogenesis is a process of formation of new blood vessels improving perfusion of a particular organ in the human body. This naturally occurring process is well documented in cancer and tumor research literature. Recently, the great variety of approaches using the principles of angiogenesis for treatment of myocardial ischemia has been under evaluation primarily for patients with diffused coronary artery disease. The aim of all these treatment methods is to promote the growth of new blood vessels to improve myocardial perfusion.

J. Anthony Ware and Michael Simons describe several possible ways to induce angiogenesis in the review article entitled "Angiogenesis in ischemic heart disease", Nature Medicine, Volume 3, Number 2, 1997, pages 158–164. They mention various growth factors that when infused in the coronary arteries, promote the growth of new vessels. Examples of such growth factors discussed in the article include the family of vascular endothelial growth factors (VGEF), also known as vascular permeability factors (VPF), various fibroblast growth factors (FGF), transforming growth factors (TGF), hepatocyte growth factors (HGF), platelet derived growth factors (PDGF), and many others. The authors point out the great variety of such agents and their possible combinations that makes it difficult at the present time to determine the best one for clinical use. Another important factor determining the success of the treatment is the delivery method. Several methods are under investigation at the present time: intravenous infusion, intra-coronary infusion, intra-pericardial infusion and intra-myocardial injection are just some examples of delivery methods under consideration.

Another group of methods use gene therapy. Genes, when injected for example in the myocardium muscle, cause the release of various growth factors that in turn promote the formation of blood vessels. Animal studies using the gene transfer of FGF-5 is described by Frank J. Giordano et al in the article entitled "intracoronary gene transfer of fibroblast growth factor-5 increases blood flow and contractile function in an ischemic region of the heart", Nature Medicine, 1996, Volume 2, Number 5, pages 534–539. Initial clinical results with the injection of the VEGF gene transfer (GTx) is described by Douglas W. Losordo et al in the article entitled "Gene therapy for myocardial angiogenesis. Initial clinical results with direct myocardial injection of phVEGF$_{165}$ as sole therapy for myocardial ischemia", Circulation, 1998, Volume 98, pages 2800–2804.

The therapeutic use for angiogenesis of the principles behind vasculogenesis, or the natural growth of blood vessels in the embryo by differentiation of angioblasts into blood islands, which then fuse to form a primitive cardiovascular system, is described by Federico Bussolino et al in the article entitled "Molecular mechanisms of blood vessel formation", TIBS, 1997, Volume 22, pages 251–256 and also by Werner Risau in the article entitled "Mechanisms of angiogenesis", Nature, 1997, Volume 386, pages 671–674.

Various angiogenic growth factor treatment methods and gene transfer methods have been described in US patents. Examples of such patents include the following: U.S. Pat. No. 5,792,453 by Hammond; U.S. Pat. No. 5,491,129 by Shatiel; U.S. Pat. No. 5,470,831 by Whitman; U.S. Pat. No. 5,318,957 by Cid; U.S. Pat. No. 5,244,460 by Unger; U.S. Pat. Nos. 4,778,787 and 4,699,788 by Catsimopoolas.

Angiogenesis may potentially be induced by means other than injection of growth factors. It is suggested in the recent literature that trans-myocardial revascularization (TMR) or catheter-based percutaneous myocardial revascularization (PMR) may prove to be a method of inducing a controlled injury to the myocardial muscle which in turn stimulates blood vessel growth and the opening of collateral vessels to perfuse the injured area of the heart. Such devices and methods are described in several US patents such as U.S. Pat. Nos. 5,840,075 and 5,725,521 by Mueller; U.S. Pat. No. 5,713,894 by Murphy—Chutorian; U.S. Pat. No. 5,672,170 by Cho; and U.S. Pat. No. 4,658,817 by Hardy.

In addition to restoring adequate blood supply, the availability of healthy myocardial cells is an important factor in restoring the contractile function of the heart. Various techniques of myocardial cell proliferation and transplantation have been suggested in the prior art to achieve that purpose. For example, U.S. Pat. Nos. 5,580,779 and 5,543,318 by Smith suggest some ways to induce proliferation of myocytes by exposing them in culture to a platelet freeze/thaw extract or by dissociation through sequential enzymatic digestion and plating on a particular growth medium selective for myocardial cell growth.

All of the above mentioned biobypass techniques as well as other techniques of similar nature have at least two common negative aspects: first, they attempt to provide for new blood vessel growth under the conditions of initially compromised coronary blood flow, and second, they take some several weeks to achieve meaningful results.

The first aspect represents a circular phenomenon: biobypass needs enough blood flow to bring the necessary elements to the treatment site. On the other hand, the blood flow was compromised initially which caused the need for biobypass in the first place. Clearly, reduction of blood flow to almost zero in some cases causes the biobypass as well as all other processes in the heat to slow down or cease completely. It would be therefore highly desirable to be able to break that cycle and create more favorable conditions for the biobypass to occur.

The second aspect is that biobypass usually takes between two and five weeks to be completed, as pointed our for example by Losordo in the above referenced article. Many cardiac patients may not be able to wait that long for the results of biobypass. There is a need therefore for a method of biobypass providing instant relief of symptoms for these patients with advanced stages of heart disease.

A new treatment method is needed therefore to address these common problems associated with biobypass techniques.

SUMMARY OF THE INVENTION

It is the object of the present invention to provide a method and a device for heart disease treatment with enhanced biobypass where the process of new vessel growth or myocardial cell proliferation is improved by increasing the coronary blood flow from the very initiation of the treatment.

It is another object of the invention to provide a method and a device for heart disease treatment which allows for immediate relief of disease symptoms while creating favorable conditions for the biobypass process to occur.

The method and the device of the present invention are based on the suggestion that increased coronary blood flow will improve the results of the biobypass therapy. According to the method of the invention, a means for increasing of coronary blood flow are provided in addition to the various methods of biobypass to achieve two purposes: improving the condition of the patient instantly after initiation of the treatment and providing better conditions for the biobypass process.

In addition or in combination with medication therapy designed to increase coronary blood flow, several known mechanical means to improve coronary blood flow may be used according to the method of the invention: implantable or extra-corporeal heart assist devices which may have pulsatile or non-pulsatile flow, external heart massage devices such as an Anstadt cup, and preferably, counterpulsation means, such as an intra-aortic balloon pumping or external counterpulsation means. Counterpulsation means are preferred because they are known to increase diastolic blood pressure and therefore increase blood flow through the coronary vessels.

DETAILED DESCRIPTION OF THE INVENTION

Biobypass is a rather complex process. It is suggested that the process of formation of new blood vessels depends at least to some degree on the supply of necessary elements such as growth factors and endothelial cell proliferation that comes from existing blood flow. Therefore, biobypass depend on the blood supply to both obtain the elements needed for the formation of new blood vessels as well as to transport away the waste products associated with normal cell function and proliferation. Should this blood supply be low or even non-existent, the formation process may be substantially imparted or even stopped.

Some authors have also suggested that blow flow has another important factor directly effecting the release of the growth factors by endothelial cells, namely the shear stress. The fact that the "wall shear stress reportedly regulates adaptive vessel growth and angiogenesis" is described by Joji Ando and Akira Kamiya in the review article entitled "Blood flow and vascular endothelial cell function", Frontiers of Medical and Biological Engineering, 1993, Volume 5, number 4, Pages 245–264.

Therefore, according to the method of the present invention it is suggested to increase the coronary blood flow as a way to stimulate the release of various growth factors and to promote the process of angiogenesis. It is believed that the combination of angiogenesis techniques with increased coronary blood flow would create the best conditions for promoting new vessel growth. The same is also true for another aspect of biobypass, namely the proliferation or transplantation of healthy myocardial cells to increase the contractility of the damaged area of the myocardium. It is believed that increased blood supply will promote better survival of transferred myocardial cells in their new environment.

Many techniques designed to increase the blood flow to the heart can be used to facilitate the method of the invention. Pharmacological support may be one of these techniques. Mechanical support in addition or as a separate method to improve the blood flow may also be considered. Various types of cardiac assist devices are known in the prior art that help to support the patient with a failing heart. They all can be used for the purposes of this invention and the choice as to which is the best device to use shall be made depending on the condition of the patient. Examples of known cardiac assist devices include various implantable and extra-corporeal pulsatile and non-pulsatile blood pumps, direct heart massage devices such as an Anstadt cup or other similar. devices described for example in the U.S. Pat. No. 5,713,954 by Rosenberg; U.S. Pat. No. 5,131,905 by Grooters; or U.S. Pat. No. 4,690,134 by Snyders; cardiomyoplasty techniques and muscle powered assist devices such as described for example in the U.S. Pat. Nos. 5,738,626 and 5,603,337 by Jarvik; U.S. Pat. No. 5,327,913 by Taheri; or U.S. Pat. No. 4,813,952 by Khalafalla.

Counterpulsation means being a separate category of cardiac assist devices represent the preferred way to practice the method of the present invention. It is well established that counterpulsation means increase diastolic blood pressure and therefore promote higher coronary blood flow. Because of that they are. believed to be of most interest for the purposes of this invention. Counterpulsation may be administered with two classes of known devices: intra-aortic balloon pumps and external counterpulsation means.

Intra-aortic balloon pumps and catheters are widely used in clinical practice today. Their design has been described in various US patents such as for example U.S. Pat. No. 5,716,373 by Wolvek or U.S. Pat. No. 4,994,018 by Saper. As opposed to other types of cardiac assist devices, they are easy to insert and the pumping can be started just minutes after the need arises. They do not require extensive surgery and are available in most hospitals treating cardiac patients. Once implanted, they are highly effective in assisting the heart of the patient by unloading the ventricle and increasing diastolic blood flow. It is not unusual to have them in place for several days or even up to a couple of weeks in some cases which may be needed for the biobypass process to occur.

External counterpulsation means such as described for example in the U.S. Pat. No. 5,554,103 by Zheng may also be used for the purposes of this invention. Although they have an important advantage of being non-invasive, their effectiveness may be not as high as with intra-aortic balloons since the therapy should be applied for not more than a couple of hours at a time.

It is important to mention in this regard that the method of the instant invention may be practiced with both continuous and intermittent cardiac assist support.

Although the present invention has been described with respect to several specific techniques and applications, it is not limited thereto. Numerous variations and modifications readily will be appreciated by those skilled in the art and are intended to be included within the scope of the present invention, which is recited in the following claims.

I claim:

1. A method for treating an ischemic host condition, said method comprising the steps of:
   a) performing a biobypass procedure, and
   b) using mechanical cardiac assist means for increasing of coronary blood flow;

wherein steps (a) and (b) are simultaneously carried out to increase said coronary blood flow during said biobypass procedure, thereby ameliorating the ischemic host condition.

2. The method as in claim 1, wherein said biobypass procedure further comprising a step of introduction of at least one growth factor.

3. The method as in claim 1, wherein said biobypass procedure is a procedure for trans-myocardial revascularization.

4. The method as in claim 1, wherein said biobypass procedure is a procedure for percutaneous myocardial revascularization.

5. The method as in claim 1, wherein said biobypass procedure is a procedure for myocardial cells proliferation.

6. The method as in claim 1, wherein said mechanical cardiac assist means for increasing of coronary blood flow being used continuously throughout the treatment time.

7. The method as in claim 1, wherein said mechanical cardiac assist means for increasing of coronary blood flow being used intermittently throughout the treatment time.

8. The method as in claim 1, wherein said mechanical cardiac assist means for increasing of coronary blood flow being a left ventricular assist device.

9. The method as in claim 1, wherein said mechanical cardiac assist means being a counterpulsation means.

10. The method as in claim 9, wherein said counterpulsation means being a means for intra-aortic balloon pumping.

11. The method as in claim 9, wherein said counterpulsation means being a means for external counterpulsation.

* * * * *